(12) United States Patent
Boon et al.

(10) Patent No.: US 6,375,945 B1
(45) Date of Patent: Apr. 23, 2002

(54) ADJUVANT COMPOSITIONS FOR VACCINES

(75) Inventors: Thierry Boon; Silvia Silla, both of Brussels; Catherine Uyttenhove, Chaumont Gistoux, all of (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 09/445,841

(22) PCT Filed: Jun. 9, 1998

(86) PCT No.: PCT/EP98/03671

§ 371 Date: Feb. 8, 2000

§ 102(e) Date: Feb. 8, 2000

(87) PCT Pub. No.: WO98/57659

PCT Pub. Date: Dec. 23, 1998

(30) Foreign Application Priority Data

Jun. 14, 1997 (GB) .............................................. 9712347

(51) Int. Cl.[7] ........................ A61K 38/19; C07K 14/475

(52) U.S. Cl. ................. 424/85.2; 424/184.1; 424/185.1; 424/450; 530/351

(58) Field of Search .............................. 424/85.2, 184.1, 424/185.1, 450; 530/351

(56) References Cited

FOREIGN PATENT DOCUMENTS

| WO | WO 94/00153 | 1/1994 |
|---|---|---|
| WO | WO 95/17209 | 6/1995 |
| WO | WO 96/10423 | 4/1996 |
| WO | WO 96/11019 | 4/1996 |
| WO | WO 97/01640 | 1/1997 |

Primary Examiner—Gary L. Kunz
Assistant Examiner—Fona Hamud
(74) Attorney, Agent, or Firm—Zoltan Kerekes; Stephen Venetianer; Charles M. Kinzig

(57) ABSTRACT

The present invention pertains to improved adjuvant compositions comprising a mixture of a saponin adjuvant such as QS21 with monophosphoryl lipid A or derivative thereof such as 3D-MPL and interleukin 12. These compositions are useful in a range of prophylactic and therapeutic applications, particularly in vaccines, including cancer vaccines.

3 Claims, 8 Drawing Sheets

Fig. 1  LUD 5482  IMMUNIZATION OF DBA/2 MICE WITH PEPTIDE P198 + DQS21/MPL ± IL12
1 OR 2 INJECTIONS s.c. footpads

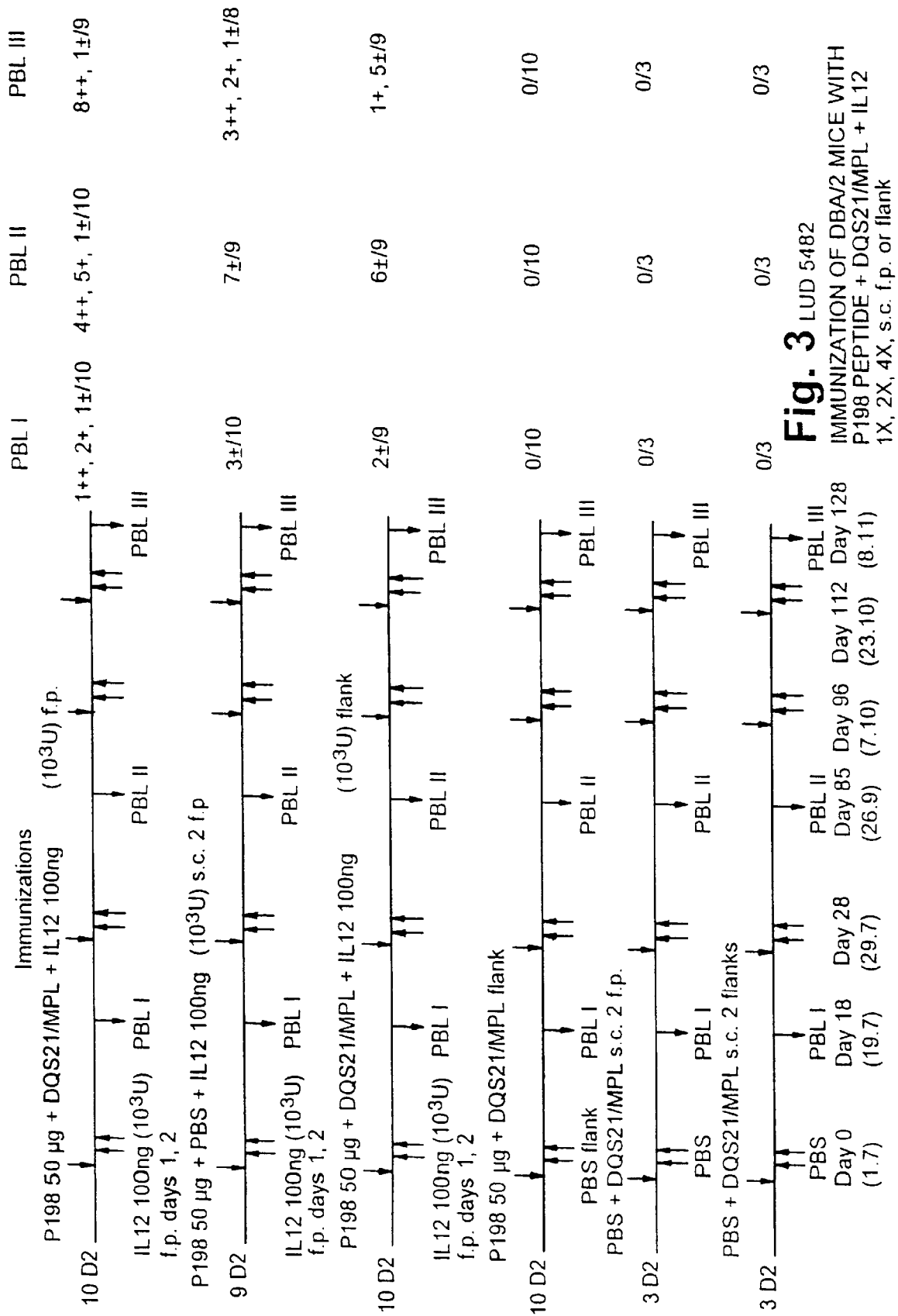
Fig. 3 LUD 5482 IMMUNIZATION OF DBA/2 MICE WITH P198 PEPTIDE + DQS21/MPL + IL12 1X, 2X, 4X, s.c. f.p. or flank

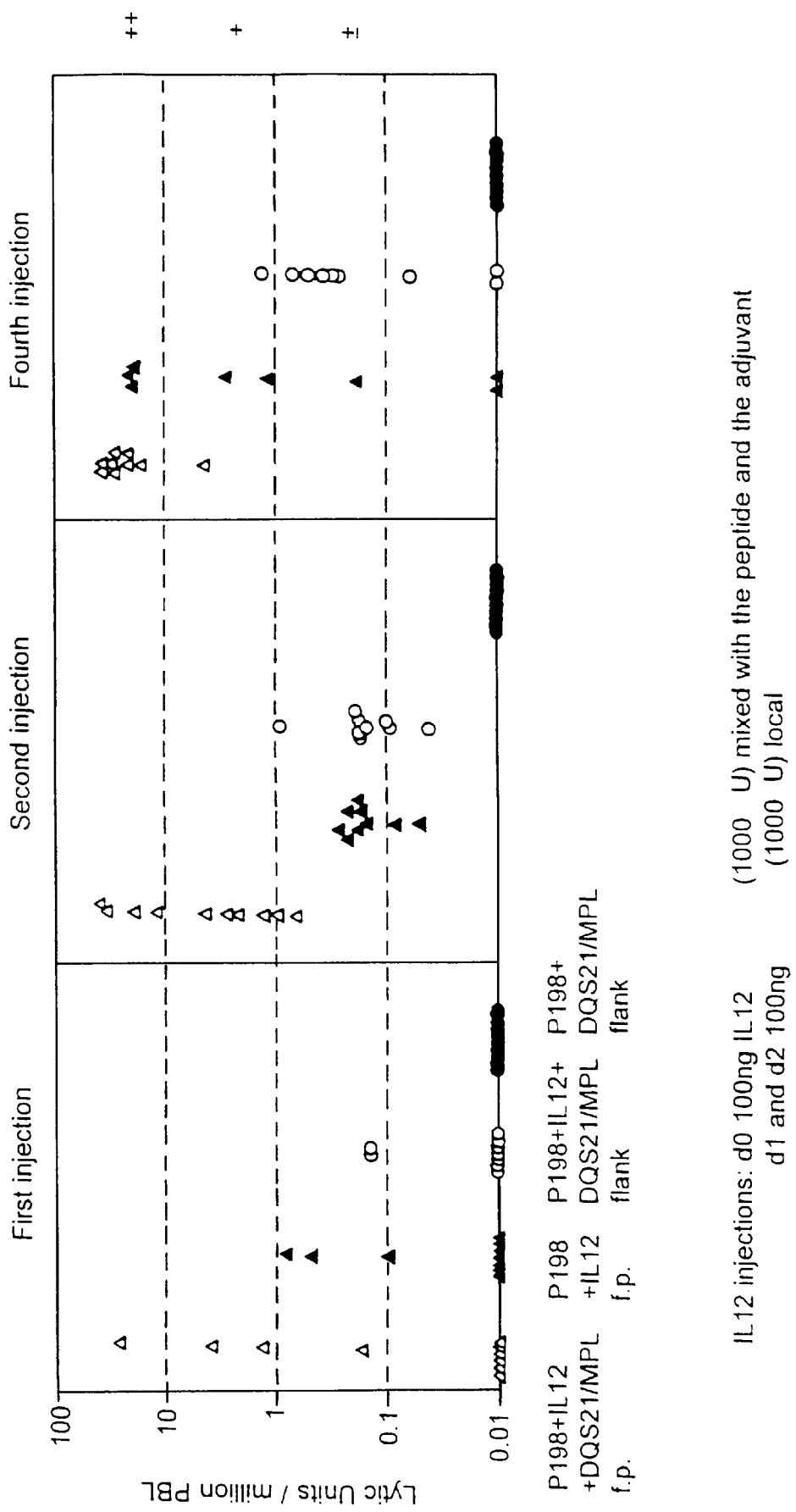

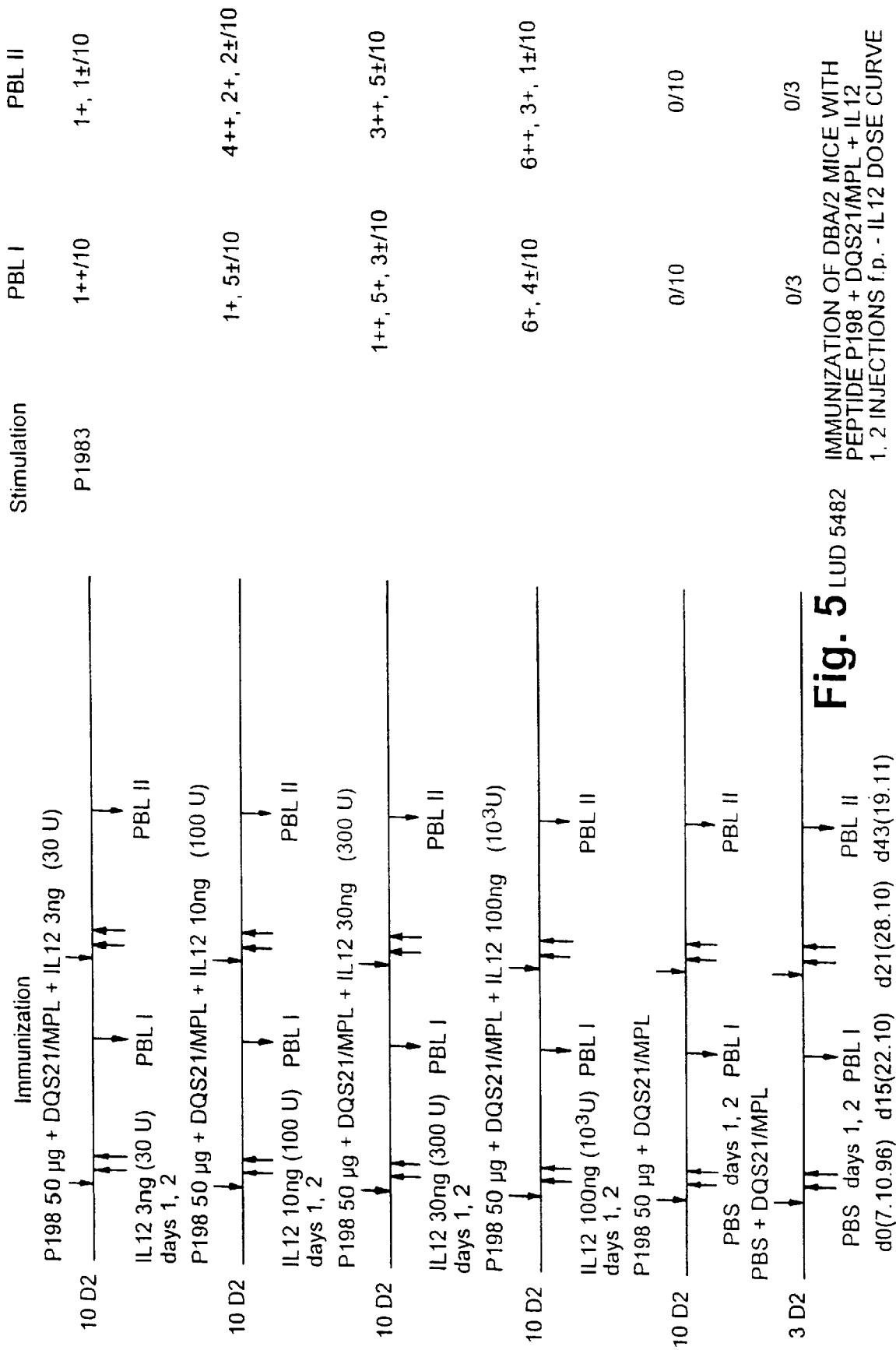

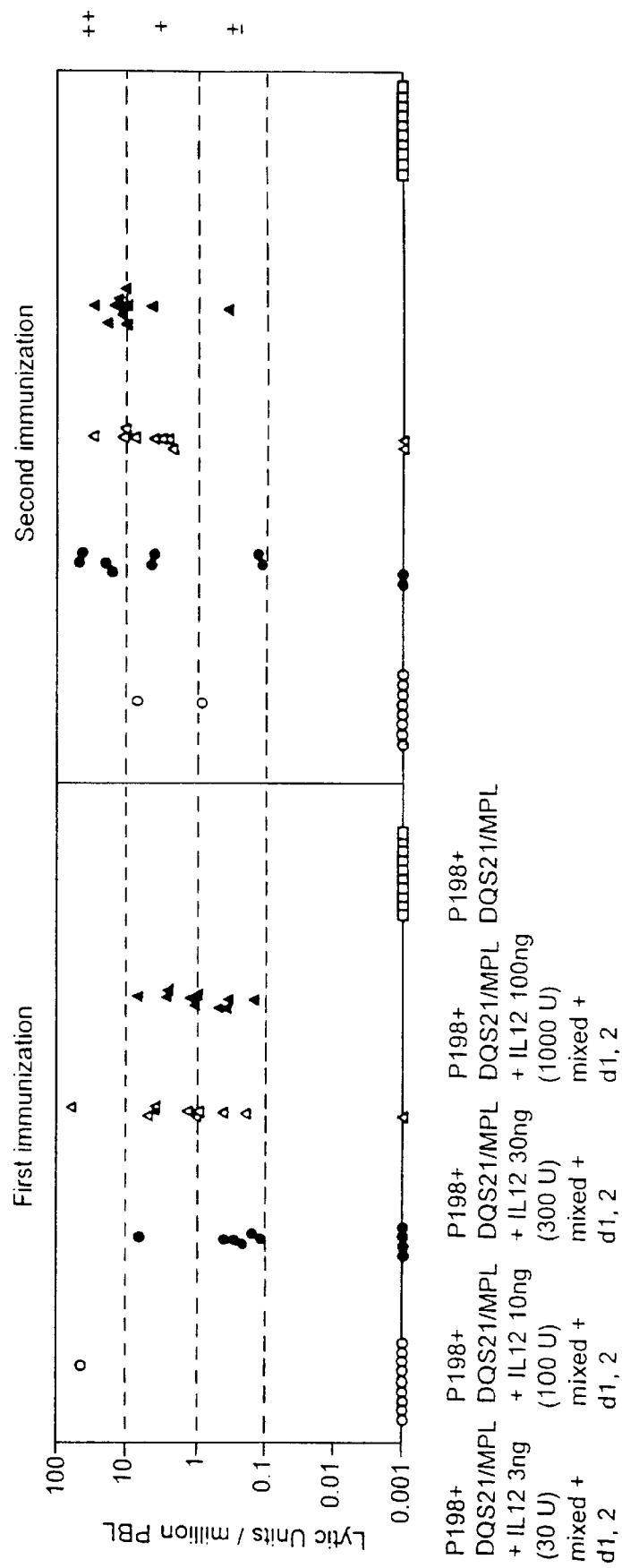
Fig. 6  LUD 5482   IL12 DOSE CURVE
IMMUNIZATION WITH PEPTIDE P198 + DQS21/MPL + IL12 f.p.

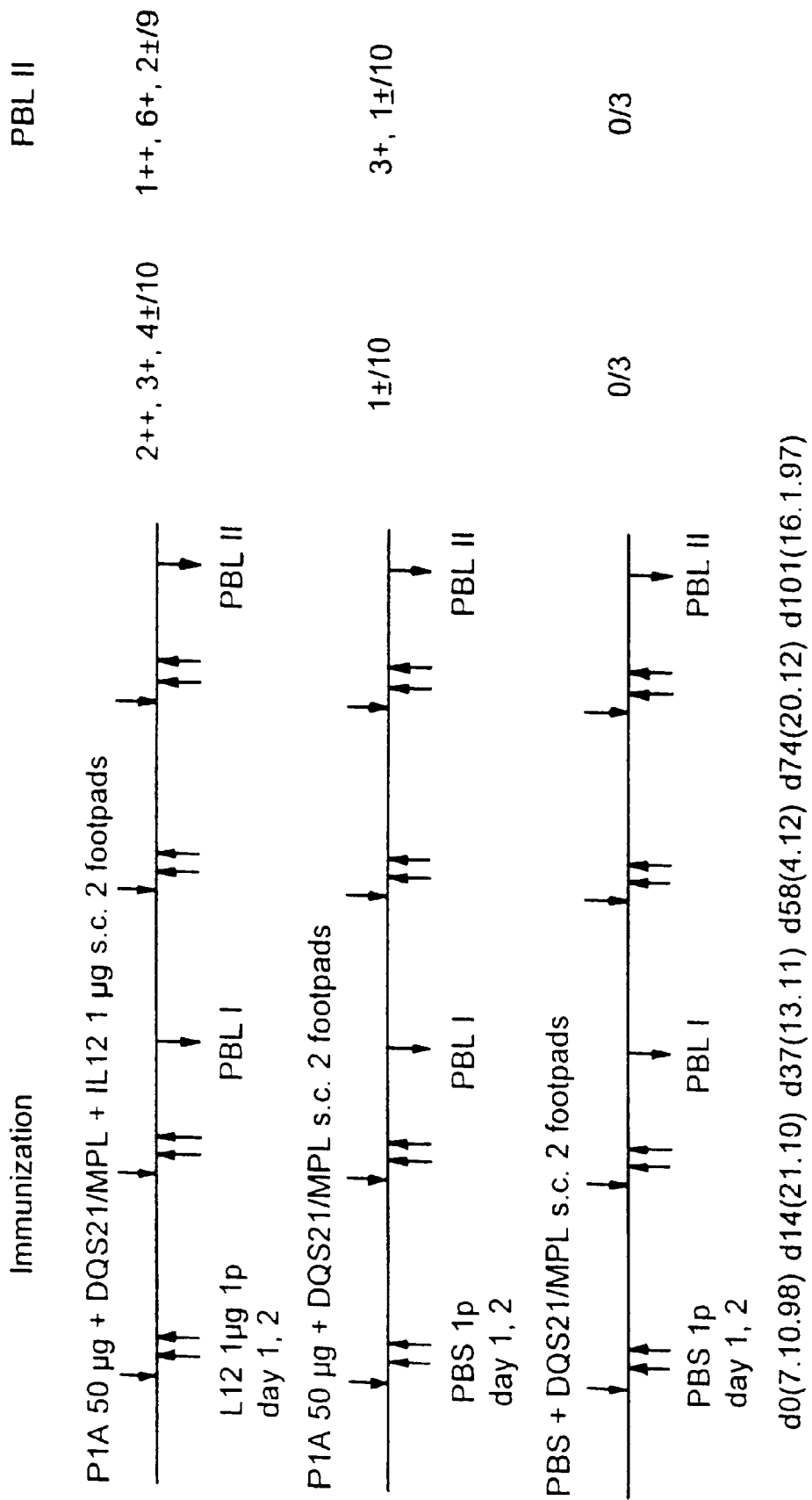
Fig. 7 LUD 5482 IMMUNIZATION OF DBA/2 MICE WITH PEPTIDE P1A + DQS21/MPL ± IL12

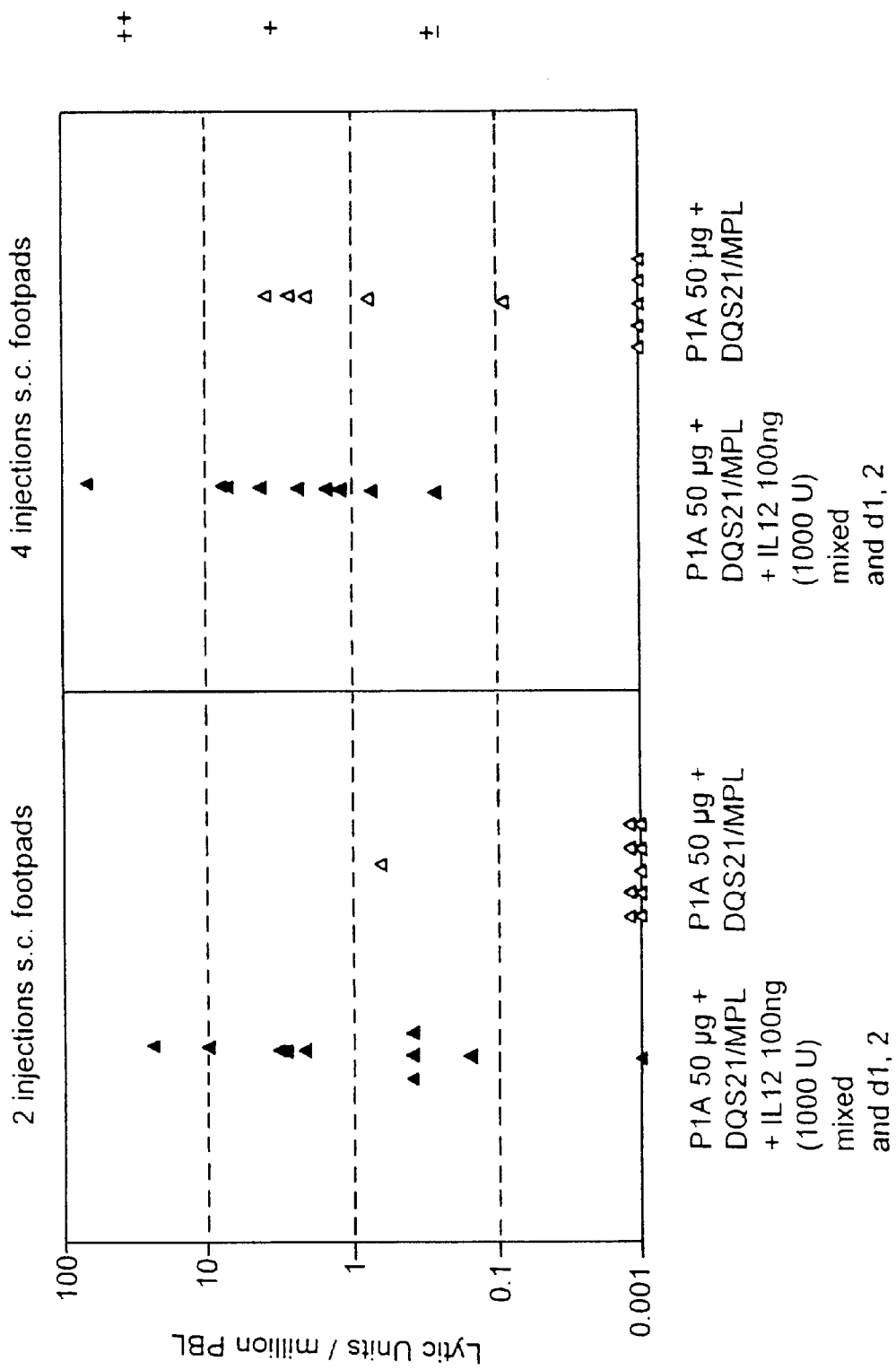
Fig. 8 LUD 5482 IMMUNIZATION OF DBA/2 MICE WITH PEPTIDE P1A + DQS21/MPL ± IL12

ADJUVANT COMPOSITIONS FOR VACCINES

CROSS-REFERENCE TO RELATED APPLICATIONS

This application is a 371 of as International Application Number PCT/EP98/03671, filed Jun. 9, 1998.

STATEMENT REGARDING FEDERALLY SPONSORED RESEARCH OR DEVELOPMENT

Not applicable.

BRIEF SUMMARY OF THE INVENTION

The present invention relates to improved adjuvant compositions, for the stimulation of an immune response suitable for immunotherapy applications. In particular the present invention relates to compositions comprising mixture of a saponin adjuvant with monophosphoryl lipid A or derivative thereof and interleukin 12. In particular, the invention relates to compositions comprising 3 de-o-acylated monosphoryl lipid A, QS21, and IL12. Such compositions are particularly useful in the immunotherapy of tumours.

BACKGROUND OF THE INVENTION

1. Field of the Invention

Cancer is a disease developing from a single cell due to genetic changes. Clinical detection of these tumours occurs mostly in a relatively late stage of disease, when the primary tumour can be removed by surgery, and the existence of micro metastases settled in different organs has often already occurred. Chemotherapy does often not completely eliminate these cells, which then remain as a source for recurrent disease.

Immune cells are able to control all different tissues (with the exception of the brain) and, due to their memory function, can also eliminate hidden cells reentering the circulation (metastasis). Therefore, an activated immune response to tumour cells is expected to be of clinical benefit. Despite their undifferentiated growth, tumour cells are in many aspects indistinguishable from normal cells, and overexpression of certain proteins or expression of mutated proteins is in most cases not sufficient to activate the immune response. This situation results in failure of immune surveillance. Thus, strategies for therapy of disseminated tumours need to specifically activate the immune response to tumour cells and to trigger migratory activity of cytotoxic T cells for example leading to elimination of most and possibly every single tumour cell. Genetic mutation in tumour cells is intense, and strong immune responses are therefore required to prevent further genetic changes of the tumour cells (escape variants) under the pressure of the immune system.

It is now well established that cellular antigens which are not cell surface proteins per se can be the targets of immune rejection through their recognition by immune regulatory and cytotoxic T cells. New potential target antigens for immune-mediated tumour rejection are being identified, based on their recognition by immune T cells, rather than by antibodies. Such antigens may or may not induce antibody formation. It is now recognized that the expression of tumour antigens by a cell is in itself not sufficient for induction of an immune response to these antigens. Initiation of a tumour rejection response requires a series of immune amplification phenomena dependent on the intervention of antigen presenting cells, which are responsible for delivery of a series of activation signals which ultimately leads to the rejection of the tumour.

Tumour rejection antigens which are presented on tumour cells and which are recognised by cytotoxic T cells can lead to lysis of the cell. To achieve this, in a clinical setting a vaccine composition comprising a rumour rejection antigen needs to be presented in a suitable adjuvant system to enable a suitable immune response to be mounted. However, activation of the immune systems requires activation signals which are initiated by antigen presenting cells and are not activated by the tumour cells themselves.

Vaccination with isolated tumour rejection antigens has been envisaged either by recombinant proteins, by the use of live recombinant vectors or by DNA vectors. Preferably subunit antigens will be used. However, to ensure these are effective, powerful adjuvant systems are required.

Accordingly, the present invention provides an adjuvant composition comprising a combination of a saponin adjuvant in combination with monophosphoryl lipid A or derivative thereof together with the cytokine Interleukin 12.

2. Description of the Related Art

Immunologically active saponin fractions having adjuvant activity derived from the bark of the South American tree Quillaja Saponaria Molina are known in the art. For example QS21, also known as QA21, is an Hplc purified fraction from the Quillaja Saponaria Molina tree and it's method of its production is disclosed (as QA21) in U.S. Pat. No. 5,057,540. Quillaja saponin has also been disclosed as an adjuvant by Scott et al, Int. Archs. Allergy Appl. Immun., 1985, 77, 409.

Monosphoryl lipid A and derivatives thereof are known in the art. A preferred derivative is 3 de-o-acylated monophosphoryl lipid A, and is known from British Patent No. 2220211.

Interleukin 12 (IL-12) is known. For a review see Trinchieri G. Interleukin-12—A proinflammatory cytokine with immunoregulatory functions that bridge innate resistance and antigen-specific adaptive immunity. Immunology 13: 251.276, 1995. It is a heterodimeric cytokine produced mostly by phagocytic cells in response to bacteria, bacterial products, and intracellular parasites, and to some degree by B lymphocytes. In particular, IL-12 is produced by antigen presenting cells and instrumental in induction of TH-1 cell responses. IL-12 induces IFN-gamma from NK and T cells, acts as a growth factor for activated NK and T cells, enhances the cytotoxic activity of NK cells, and induces cytotoxic T lymphocyte generation.

BRIEF DESCRIPTION OF THE DRAWINGS

FIG. 3 shows a modified immunisation protocol whereby DBA/2 mice are immunised with peptide 198 adjuvanted or not with DQS21/3D-MPL and with or without addition of IL-12. One to four injections are delivered subcutaneously intra footpads or in the flanks, following which CTL activity was measured.

FIG. 4 shows the CTL activity, as measured in lytic units per million lymphocytes, following one to four immunisations of DBA/2 mice with peptide 198 adjuvanted or not with DQS21/3D-MPL and with or without addition of IL-12.

FIG. 5 shows the immunisation protocol whereby DBA/2 mice are immunised with peptide 198 adjuvanted with DQS21/3D-MPL and with increasing doses of IL-12. One or two injections are delivered subcutaneously intra footpads, following which CTL activity (IL-12 dose curve) is measured.

FIG. 6 shows the CTL activity (IL-12 dose curve), as measured in lytic units per million lymphocytes, following one to two immunisations of DBA/2 mice with peptide 198 adjuvanted with DQS21/3D-MPL-and with increasing doses of IL-12.

FIG. 7 shows the immunisation protocol whereby DBA/2 mice are immunised up to four times with peptide P1A adjuvanted with DQS21/3D-MPL and with or without IL-12. The injections are delivered subcutaneously intra footpads, following which CTL activity was measured.

FIG. 8 shows the CTL activity (IL-12 dose curve), as measured in lytic units per million lymphocytes, following immunisation of DBA/2 mice with peptide P1A adjuvanted with DQS21/3D-MPL and with or without IL-12.

Figure 1:
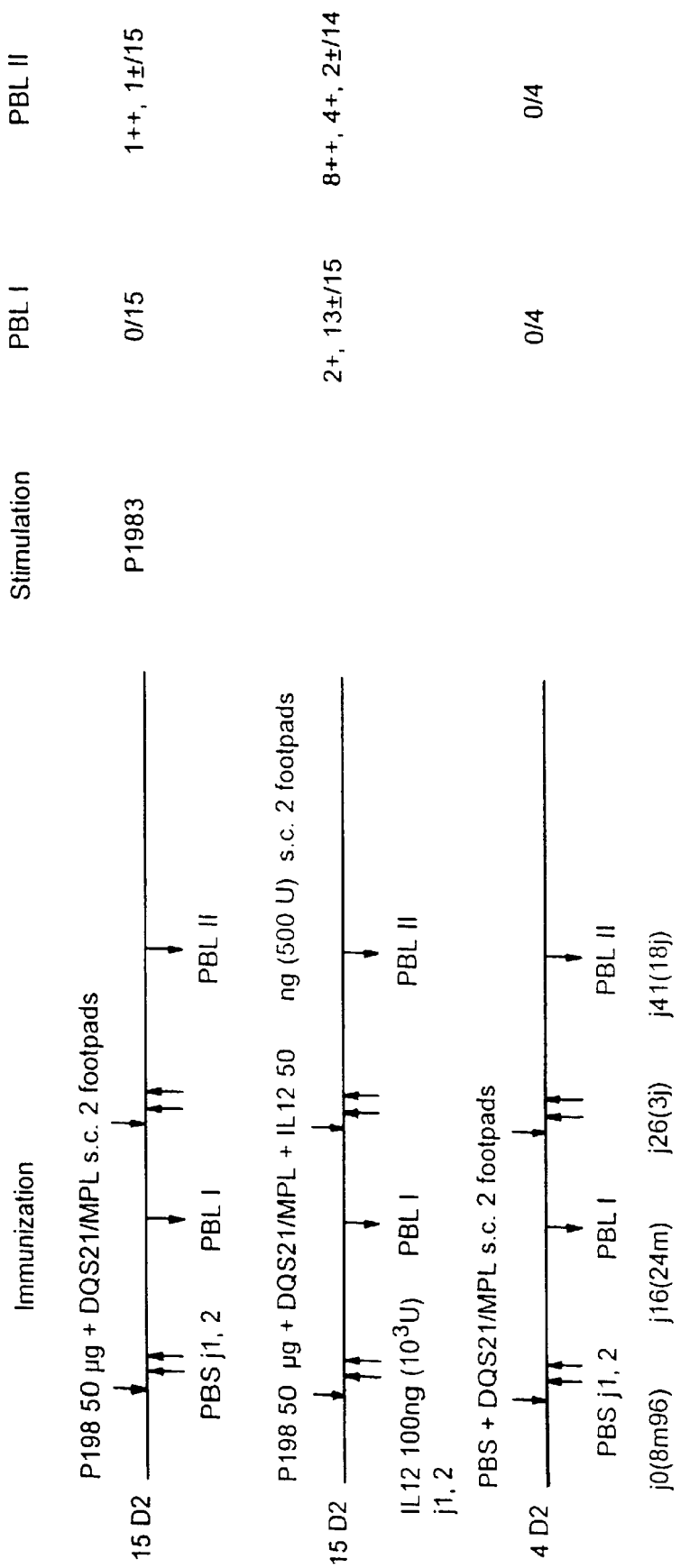
FIG. 1 shows the immunisation protocol whereby DBA/2 mice are immunised with peptide 198 adjuvanted or not with DQS21/3D-MPL and further adjuvanted with IL-12. One or two injections are delivered subcutaneously intra footpads, following which CTL activity was measured.

IL-12 and IL-12-induced IFN-gamma favor Th1 cell differentiation by priming CD4 (+) T cells for high IFN-gamma production. However, we surprisingly found that other cytokines, such as IFN-γ, IL-2, IL-6, IL-7, GM-CSF or MCP were unable to enhance the effect of the QS21/MPL adjuvant.

Preferably the compositions of the invention contain immunologically active saponin fraction in substantially pure form. Preferably the compositions of the invention contain QS21 in substantially pure form, that is to say, the QS21 is at least 90% pure, preferably at least 95 % pure and most preferably at least 98% pure. Other immunologically active saponin fractions useful in compositions of the invention include QA17/QS17.

In a preferred embodiment the composition also comprises a sterol such as cholesterol wherein the sterol is present in an excess ratio to that of the saponin. These show decreased reactogenicity when compared to compositions in which the cholesterol is absent, while the adjuvant effect is maintained. In addition it is known that QS21 degrades under basic conditions where the pH is about 7 or greater. Thus a further advantage is that the stability of QS21 to basemediated hydrolysis is enhanced in formulations containing cholesterol.

Although the adjuvant compositions can be utilised for the treatment or prophylaxis of a range of disease, they find particular utility in the field of cancer immunotherapy.

In particular, the adjuvant formulation finds utility particularly with tumour rejection antigens such as those for prostrate, breast, colorectal, pancreatic, renal or melanoma cancers. Exemplary antigens include MAGE 1 and MAGE 3 or other MAGE antigens for the treatment of melanoma, BAGE or GAGE LAGE (NY-eso-1) PRAME or Her-2/neu; Robbins and Kawakami (1996), Current Opinions in Immunology 8, pps 628–636; Van den Eynde et al., International Journal of Clinical & Laboratory Research (submitted 1997); Correale et al. (1997). Journal of the National Cancer Institute 89, p293. Indeed these antigens are expressed in a wide range of tumour types such as melanoma, lung carcinoma, sarcoma and bladder carcinoma. Other classes of antigens useful in the context of the present invention include tissue specific antigens such as Prostate Specific antigen (PSA); Prostate Specific Membrane antigen (PMSA), Melan A/Mart 1, gp100, tyrosinase TRP1 or TRP2.

Accordingly in one aspect of the present invention there is provided a vaccine comprising an adjuvant composition according to the invention and a tumour rejection antigen, or tissue specific antigen.

Other antigens or antigenic compositions include for example, polysaccharide antigens, protein antigens or DNA encoding antigens or antigenic compositions derived from HIV-1, (such as gp120 or gp160), any of Feline Immunodeficiency virus, human or animal herpes viruses, such as gD or derivatives thereof or Immediate Early protein such as ICP27 from HSV1 of HSV2, cytomegalovirus (especially human) (such as gB or derivatives thereof), Varicella Zoster Virus (such as gpI, II or III), or from a hepatitis virus such as hepatitis B virus for example Hepatitis B Surface antigen or a derivative thereof, hepatitis A virus, hepatitis C virus and hepatitis E virus, of from other viral pathogens, such as Respiratory Syncytial virus (for example RSV F and G proteins or immunogenic fragments thereof disclosed in U.S. Pat. No. 5,149,650 or chimeric polypeptides containing immunogenic fragments from HSRV proteins F and G, eg GF glycoprotein disclosed in U.S. Pat. No. 5,194,595), antigens derived from meningitis strains such as meningitis A, B and C, Streptococcus Pneumonia, human papilloma virus, in particular from strains HPV6, 11, 16 and 18, Influenza virus, Haemophilus Influenza B (Hib), Epstein Barr Virus (EBV), or derived from bacterial pathogens such as Salmonella, Neisseria, Borrelia (for example OspA or OspB or derivatives thereof), or Chlamydia, or Bordetella for example P.69, PT and FHA, or derived from parasites such as plasmodium or toxoplasma.

The P815 tumour is a mastocytoma, induced in a D BA/2 mouse with methylcholanthrene and cultured as both an in vitro tumour and cell line. This represents an excellent model system for the human.

The model system described in this application is a murine system whereby a murine tumour antigen, P1A, expressed in the mouse mastocytoma P815, is being tested for its ability to stimulate CTL in the mouse with and without adjuvant. The significance of this system is that P1A is a true tumour rejection antigen in that its gene is the same in both normal and tumour cells but the gene is silent in normal cells and only expressed in tumour cells. This is in comparison to other P815 antigens that were previously found and which are created by mutation of normal alleles. These are called tum- variants or tum- antigens. Mutations in the tum-antigens create new antigenic peptides which can then be recognised by CTL.

Turn- antigens are likely to be tumour-specific whereas true tumour antigens will be shared between different tumours and patients and therefore the latter will be better candidates for vaccine formulations. Human tumour rejection antigens analogous to P1A include the MAGE, BAGE, GAGE etc. families as described earlier. These genes are found in both normal and tumour tissues but the corresponding proteins are expressed only in tumours and in normal testis. As the testis is an immune privileged site it is unlikely to be affected by any vaccine.

P1A is a true murine TRAs. Therefore, one can test a large number of adjuvants with a variety of different assays in mice giving a good indication as to which formulations should be used with human tumour rejection antigens in human clinical trials.

Preferred compositions of the invention are those forming a liposome structure. Compositions where the sterol/ immunologically active saponin fraction forms an ISCOM structure also form an aspect of the invention.

The ratio of QS21: sterol will typically be in the order of 1:100 to 1:1 weight to weight. Preferably excess sterol is present, the ratio of QS21:sterol being at least 1:2 w/w. Typically for human administration QS21 and sterol will be present in a vaccine in the range of about 1 ng to about 100 µg, preferably about 10 µg to about 50 µg per dose.

The liposomes preferably contain a neutral lipid, for example phosphatidylcholine, which is preferably non-crystalline at room temperature, for example eggyolk phosphatidylcholine, dioleoyl phosphatidylcholine or dilauryl phosphatidylcholine. The liposomes may also contain a charged lipid which increases the stability of the lipsome-QS21 structure for liposomes composed of saturated lipids. In these cases the amount of charged lipid is preferably 1–20% w/w, most preferably 5–10%. The ratio of sterol to phospholipid is 1–50% (mol/mol), most preferably 20–25%.

The compositions of the invention also contain a 3 deacylated monophosphoryl lipid A derivative (3-de-o-acylated monophosphoryl lipid A, also known as 3D-MPL) and is manufactured by Ribi Immunochem, Montana. A preferred form is disclosed in International Patent Application 92/116556.

Suitable compositions of the invention are those wherein liposomes are initially prepared without 3D-MPL, and 3D-MPL is then added, preferably as 100 nm particles. The 3D-MPL is therefore not contained within the vesicle membrane (known as 3D-MPL out). Compositions where the 3D-MPL is contained within the vesicle membrane (known as 3D-MPL in) also form an aspect of the invention. The antigen can be contained within the vesicle membrane or contained outside the vesicle membrane or encapsulated. Preferably soluble antigens are outside and hydrophobic or lipidated antigens are either contained inside or outside the membrane. The 3D-MPL will be present in the range of about 1 Ug to 100 Ug and preferably about 10 to 50 µg per dose of human vaccine.

Often the vaccines of the invention will not require any specific carrier and formulated in an aqueous or other pharmaceutically acceptable buffer. In some cases it may be advantageous that the vaccines of the present invention will further contain alum.

EXAMPLE 1 a)—Immunisation of DBA/2 mice with peptide+3 D-MPL+QS21+Lipids±IL12

Human tumours express antigens that can be recognized by autologous CTL. These antigens constitute useful targets for cancer immunotherapy. We decided to evaluate in the P815 murine mastocytoma model the efficacy of an immunization method that could be applied to human patients. Syngeneic DBA/2 mice were injected with antigenic peptides mixed with adjuvant and murine IL12.

An adjuvant composition comprising QS21, lipids (DQ) and 3 de-o-acylated monophosphoryl lipid A (3D-MPL) was prepared.

Briefly a mixture of lipid (such as phosphatidylcholine either from egg-yolk or synthetic) and cholesterol in organic solvent, is dried down under vacuum (or alternatively under a stream of inert gas). An aqueous solution (such as phosphate buffered saline) is then added, and the vessel agitated until all the lipid is in suspension. This suspension is then microfluidised until the liposome size is reduced to 100 nm, and then sterile filtered through a 0.2 Um filter. Extrusion or sonication could replace this step.

The cholesterol phosphatidylcholine ratio is 1:4 (w/w), and the aqueous solution is added to give a final cholesterol concentration of 5 to 50 ng/ml. The liposomes have a defined size of 100 nm and are referred to as SUV (for small unilamellar vesicles). If this solution is repeatedly frozen and thawed the vesicles fuse to form large multilamellar structures (MLV) of size ranging from 500 mn to 15 µm.

QS21 in aqueous solution is added to the liposomes. This mixture is then added to 50 µg of P198 peptide (KYQAVTTTL) and 3D-MPL.

FIG. 1 Immunisation of DBA/2 Mice with Peptide p198±DQS21/3D-MPL±IL12

DBA/2 mice were injected s.c. in the two footpads with 50 µg of P198 peptide (KYQAVTTTL), corresponding to the antigen expressed by the P198 TUM—clone (Sibille et al., J. Exp. Med., 1990: 172, 35–45), mixed with the DQS21/3D-MPL adjuvant (adjuvant) 100 µl final. For a second group of animals we added to the peptide and adjuvant solution 50 ng (500U) murine IL12. This murine IL12 was purified from the supernatant of transfected P1HTR cells as described in Gajewski et al. (J. Immunol. 1995, 154: 5637–5648). On d1 and 2, we injected locally an additional dose of IL12 100 ng (1000U) or PBS. On day 16, the mice were bled and stimulation of blood lymphocytes was performed by mixing $3 \times 10^5$ Ficoll purified lymphocytes with 1 irradiated stimulating cells (100 Gy) and $2 \times 10^6$ irradiated normal syngeneic spleen cells (30 Gy) as feeder cells. The stimulating cells were P1983 cells, an azaguanine-resistant variant derived from the P198 TUM-clone. The cells were incubated in 48-well plates in a final volume of 0,8 ml MLTC medium described in Warnier et al. (Int. J. Cancer, 1996, 67, 303–310). Seven days later, CTL activity was measured in a standard chromium-release assay using 1,000 $5^1$Cr-labelled targets. Two targets were used:the P1983 cells or the P511 cells (azaguanine-resistant variant derived from the P815 TUM+cells) not expressing the P198 antigen. To eliminate non-specific lysis, $10^5$ cold P511 cells were added as competitors. On day 26, the mice received a second injection of peptide, adjuvant and IL12 or PBS, followed by two local injections of 100 ng (1000U) IL12 or PBS. A second bleeding of the mice was performed on day 41 to estimate CTL activity after two injections. Data are expressed in lytic units (LU)/$10^6$ lymphocytes as described in Brichard et al. (Eur. J. Immunol., 1995, 25: 664–671). Specific lytic units were calculated by subtracting the values obtained with the negative targets (usually less than 0,3 LU) from those obtained with the positive target. Mice were scored as ± when the LU detected were comprised between 0,1 and 1; + when LU were comprised between 1 and 10; and ++ above 10 LU.

Figure 2:
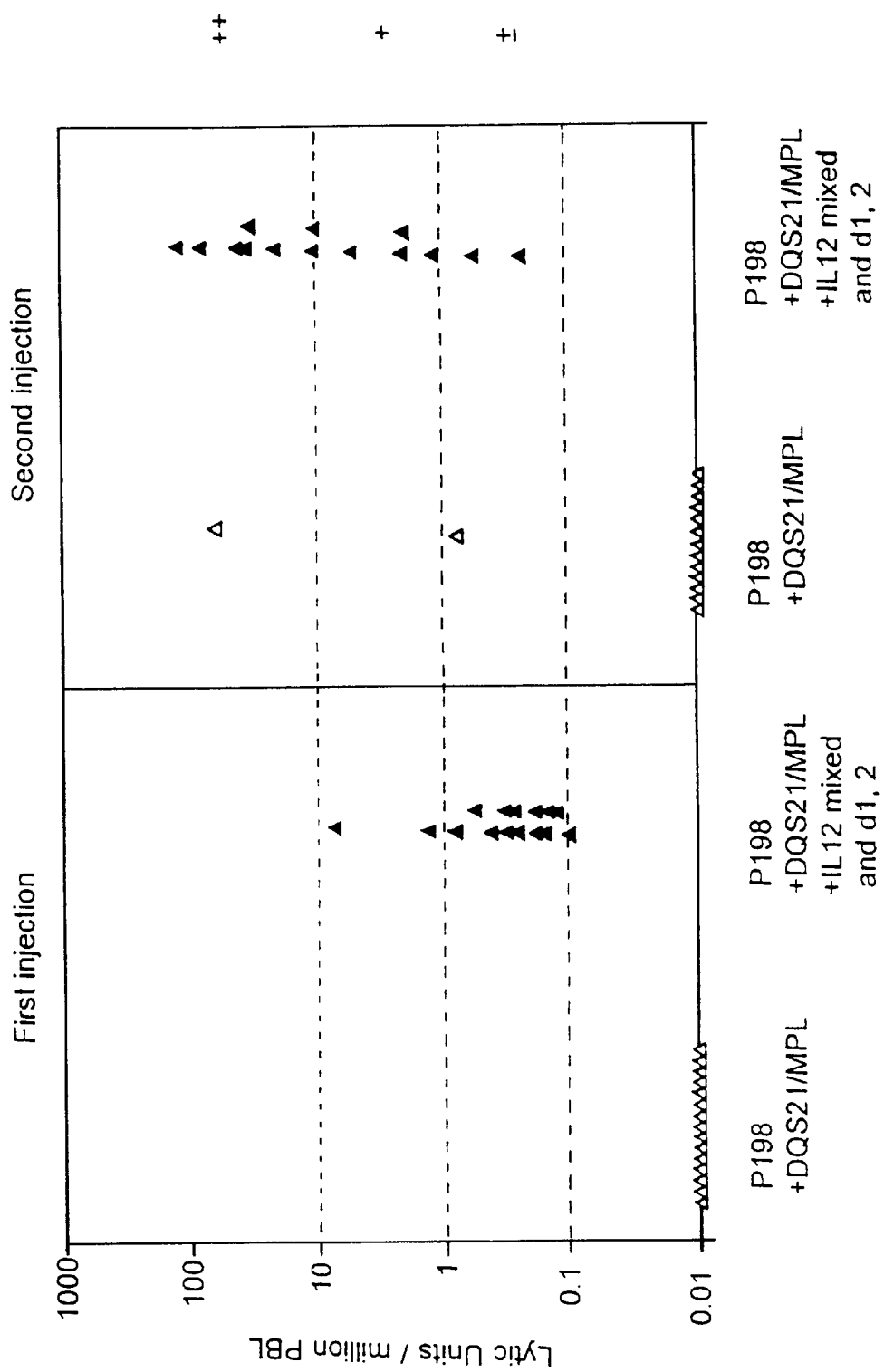
FIG. 2 shows the CTL activity, as measured in lytic units per million lymphocytes, following one or two immunisations of DBA/2 mice with peptide 198 adjuvanted with DQS21/3D-MPL with or without addition of IL-12.

FIG. 2 CTL Activity in Mice Injected with Peptide P198±DQS21/3D-MPL±IL12

After the first injection, no CTL activity was detected in the mice injected with the peptide and the adjuvant. When IL12 was added significant CTL activity was detected in all the animals. For the majority of the mice (13/15) the response was moderate since we measured less than 1 LU/$10^6$ PBL. After the second immunization, two mice out of 15, injected with the peptide and adjuvant alone were positive. In the group injected with IL12, CTL activity had increased and half of the mice showed a very high response. The addition of IL12 to the peptide and the adjuvant increased strongly the number of responding mice and the level of CTL activity observed after only a few injections.

FIG. 3 Immunisation of DBA/2 Mice with Peptide
P198±DQS21/3D-MPL±IL12 in Footpads or
Flanks.

In this second experiment, we applied the immunisation protocol described before (FIG. 1) with some modifications. To determine the relative contribution of IL12 and adjuvant in CTL induction, we injected one group of mice in the footpads with P198 peptide and IL12 without adjuvant. To test a s.c. injection site that is applicable to humans, we also injected 2 groups of mice s.c. in the flank instead of the footpads; the first one receiving the peptide, the adjuvant and the IL12 and the second receiving only the peptide and the adjuvant. Four injections were performed and mice were bled after the first, the second and the fourth injection for CTL activity determinations.

FIG. 4 CTL Activity in Mice Injected with Peptide
P198±DQS21I3D-MPL±IL12 in the Footpads or
the Flanks.

After the first immunisation, we observed that 4 mice out of 10 injected with peptide, the adjuvant and IL12 in the footpads showed a significant CTL activity. In the group injected without adjuvant 3 mice also showed CTL activity but the response was lower. Nearly no response was obtained after injection into the flanks since only 2 mice receiving the peptide, the adjuvant and IL12 showed a weak CTL activity.

After the second immunisation, all the mice receiving the peptide, the adjuvant and IL12 combination in the footpads exhibited high CTL activity. All the mice injected with the peptide and the IL12 without adjuvant also showed a specific CTL activity, but much weaker. The same situation is observed for the mice injected in the flank with the peptide, the adjuvant and the IL12 while in the absence of IL12 no response is observed after injection in the flank. After the fourth injection, all the mice that received peptide. adjuvant and IL12 in the footpads had a CTL activity located in the high values. We also observed an increase in the average of CTL activity for the mice injected without adjuvant or receiving the peptide, the adjuvant and the IL12 in the flank. Even after 4 injections we did not observe any response in the mice injected in the flank without IL12.

We confirm in this experiment the potent effect of IL12 on the generation of CTL activity after immunisation with the P198 peptide. This effect is enhanced by the combination with the DQS21/3D-MPL adjuvant since the response is obtained earlier in all the mice and since the average level of response is higher. The effect of IL12 is also required to obtain CTL activity when the antigen is injected in the flank instead of in the footpads.

FIG. 5 IL12 Dose Curve

Mice were injected with the P198 peptide mixed with the DQS21/3D-MPL adjuvant. Different doses of murine IL12 3 ng (30U), 10 ng (100U), 30 ng (300U), 100 ng (1000U) were mixed with the peptide and the adjuvant and also repeated locally the two following days. The control group received the peptide and the adjuvant but no IL12. Mice were bled after each of the two immunisations to monitor the appearance and level of CTL activity.

FIG. 6 CTL Activity in Mice Receiving Peptide
P198±DQS21/3D-MPL±Various Doses of IL12

In the two preceding experiments we used a high dose of IL12 (1 µg/mouse/day). Even if the IL12 was injected locally we saw a systemic toxicity with symptoms similar to those observed in a LPS shock. We decided to try decreasing doses of IL12. The effect of IL12 was nearly fully maintained when the dose/mouse/day was decreased to 10 ng (100U). It disappeared when the mice were injected with only 30 ng IL12. At that dose, the systemic toxicity of IL12 was largely reduced but not totally absent.

FIG. 7 Immunisation of DBA/2 Mice with Peptide
P1 A±DQS21/3D-MPL±IL12

After several experiments with the peptide P198 showing that high CTL activity were induced by injections of a combination of peptide, adjuvant and IL12, we decided to apply this protocol to the P1A peptide. This peptide presented by the Ld molecule constitutes the P815A antigen that is a major target for the immune rejection in vivo (Uyttenhove et al. J. Exp. Med., 1983, 157:1040–1052). Gene P1A, which code for the P815A antigen is expressed in several mastocytoma tumour lines (Van den Eynde et al. J. Exp. Med., 1991, 173: 1373–1384). Like the MAGE, BAGE and GAGE genes, it is not expressed in adult normal tissues, with the exception of spermatogonia in the testis (Van den Eynde et al, 1991 and Uyttenhove et al, Int. J. Cancer, 1997, 70: 349–356). Accordingly, the P815A antigen represents a good mouse model for the human MAGE, BAGE and GAGE antigens.

Mice were injected s.c. in the two footpads with 50 µg of P1A peptide (LPYLGWLVF described in Lethé et al. Eur. J. Immunol. 1992, 22: 2283–2288) mixed with the adjuvant DQS21/3D-MPL. For one group, 100 ng (1000U) of IL-12 was added to the peptide and the adjuvant. These mice received additional doses of 100 ng (1000U) IL-12 injected locally the two following days. This injection scheme was repeated four times and the mice were bled after the second and the fourth injection. The lymphocytes were restimulated in vitro for 7 days and the CTL activity was measured in a conventional[51] Cr assay. We used L1210. P1A cells as stimulating cells. The syngeneic L1210 P1A transfectant cells expressing the antigen P815AB were generated as described in Uyttenhove et al. Int. J. Cancer (1997) 70: 349–356. As target cells we used P511 cells expressing all the P815 antigens and P1-204 cells, an antigen-loss variant not expressing the P815 AB antigen described in Uyttenhove et al (J. Exp. Med., 157, 1040–1052, 1983). To avoid problems of non specific lysis, cold P1-204 were added as competitors.

FIG. 8 CTL Activity in Mice Injected with the P1A
Peptide±DQS21/3D-MPL±IL12

After two injections, 9 mice out of ten showed significant CTL activity specific for the P815A antigen when IL12 was added to the peptide and adjuvant. Half of those mice exhibited high CTL activity levels. In the group injected without IL12, a positive response was detected only in one mouse and this activity was rather low.

After the fourth injection, all the mice receiving IL12 were positive and the average of lytic units had increased. Without IL12 we detected a good CTL activity in four mice, one addition al mouse showed a very low response at the limit of the significance threshold. In this system again, the addition of L12 increased the number of responding mice and diminished the number of injections needed to obtain high and specific CTL activity. In this experiment we injected a high dose of IL12 (100 ng (1000U)/mouse/day). Like in the previous experiments using the P198 peptide we observed systemic toxic effects of the IL12.

Conclusion:

The addition of IL12 to peptide and adjuvant combination is very effective at increasing the number of mice displaying high CTL responses after immunisation. In addition, CTL responses appear earlier in the presence of IL12.

What is claimed is:

1. An adjuvant compostion comprising a saponin adjuvant selected from the group consisting of QS-21 and QS-17, further comprising 3-O-deacylated monophosphoryl lipid A and Interleukin 12.

2. An adjuvant composition as claimed in claim 1 additionally comprising cholesterol.

3. A method of producing an adjuvant compostion as claimed in claim 1 comprising admixing a saponin adjuvant selected from the group consisting of QS-21 and QS-17, further comprising 3-O-deacylated monophosphoryl lipid A and Interleukin 12.

* * * * *